(12) United States Patent
Nishiuchi

(10) Patent No.: US 8,507,727 B2
(45) Date of Patent: Aug. 13, 2013

(54) METHOD FOR PRODUCING CYCLOHEXYL ALKYL KETONES

(75) Inventor: Junya Nishiuchi, Okayama (JP)

(73) Assignee: Mitsubishi Gas Chemcial Company, Inc., Tokyo (JP)

( * ) Notice: Subject to any disclaimer, the term of this patent is extended or adjusted under 35 U.S.C. 154(b) by 0 days.

(21) Appl. No.: 13/496,569

(22) PCT Filed: Sep. 16, 2010

(86) PCT No.: PCT/JP2010/066078
§ 371 (c)(1),
(2), (4) Date: Mar. 16, 2012

(87) PCT Pub. No.: WO2011/034144
PCT Pub. Date: Mar. 24, 2011

(65) Prior Publication Data
US 2012/0178970 A1    Jul. 12, 2012

(30) Foreign Application Priority Data

Sep. 18, 2009  (JP) ................................. 2009-217202

(51) Int. Cl.
*C07C 45/62*    (2006.01)
(52) U.S. Cl.
USPC ....................................................... 568/350
(58) Field of Classification Search
USPC ....................................................... 568/350
See application file for complete search history.

(56) References Cited

FOREIGN PATENT DOCUMENTS

| | | |
|---|---|---|
| JP | 61 260032 | 11/1986 |
| JP | 10 45646 | 2/1998 |
| JP | 2005 187352 | 7/2005 |

OTHER PUBLICATIONS

Rouzaud, J., et al., "Transpositons d'hydroxy-I cyclohexylcarbinols et des cetones isomeres correspondantes, (1$^{st}$ Memoire) synthese d'hydroxyl-I cyclohexyl carbinols," Memoires Presentes a La Societe Chimique, No. 469, pp. 2908-2916 (Jun. 10, 1964).
Doucet, J., et al., "Influence de la ramification du philodiene sur la reaction de Diels-Alder avec le butadiene et ses derives," Memoires Presentes a La Societe Chimique, No. 118, pp. 610-613 (May 22, 1952).
Harris, E.E., et al., "Reaction of Hardwood Lignin with Hydrogen," A Communication from the United States Forest Products Laboratory, pp. 1467-1470, (Jun. 1938).
International Search Report Issued Oct. 19, 2010 in PCT/JP10/66078 Filed Sep. 16, 2010.

*Primary Examiner* — Sikarl Witherspoon
(74) *Attorney, Agent, or Firm* — Oblon, Spivak, McClelland, Maier & Neustadt, L.L.P.

(57) ABSTRACT

Provided is an industrially superior method for producing cyclohexyl alkyl ketones, which solves the problems in process reduction and in disposal of wastes such as metals.
An aromatic ketone represented by a formula (1) is nuclear-hydrogenated with pressurized hydrogen and in the presence of a solvent at a temperature of from 20 to 120° C., in the presence of a catalyst that carries from 0.1 to 20% by weight of a ruthenium atom on the carrier, thereby producing a cyclohexyl alkyl ketone represented by a formula (2): provided that, in the formula (2), n indicates an integer of from 1 to 3; R represents a hydroxyl group, a cyclohexyl group, an alkyl group having from 1 to 4 carbon atoms, or an acyl group having from 1 to 4 carbon atoms

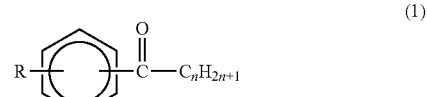

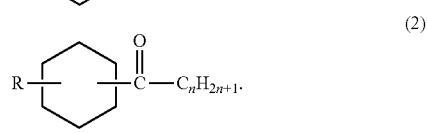

12 Claims, No Drawings

METHOD FOR PRODUCING CYCLOHEXYL ALKYL KETONES

TECHNICAL FIELD

The present invention relates to a production method excellent in selectivity for saturated aliphatic ketones having cyclohexane ring (occasionally abbreviated as cyclohexyl alkyl ketones) useful as various starting materials in industrial chemistry and as starting materials for production of medicines, agricultural chemicals, optical functional materials and electronic functional materials.

BACKGROUND ART

Heretofore, as a method for producing cyclohexyl alkyl ketones, there is known a method of obtaining them from a Grignard reagent synthesized from bromocyclohexenes, and a fatty acid chloride (see Non-Patent Document 1). Also known is a method of obtaining them by synthesizing cyclohexanecarbonitrile followed by similarly reacting it with ethylbromomagnesium (see Non-Patent Document 2). However, the above-mentioned prior-art technique has some problems in that the process is long and the disposal of wastes such as metal salts and others is difficult. In addition, in case where an aromatic ketone is hydrogenated with pressurized hydrogen according to the prior-art technique (see Non-Patent Document 3), the process involves a drawback in that not cyclohexyl alkyl ketones but aliphatic alcohols or alkylcylohexanes are synthesized as a result of reduction of the carbonyl group. Further, Patent Document 1 describes a method of producing a cyclohexyl alkyl ketone in which the cyclohexyl group has an alkyl substituent, as a result of hydrogenation of a phenyl alkyl ketone in which the phenyl group has an alkyl substituent; however, the yield in this method is about 30% and is low.

PRIOR ART DOCUMENT

Patent Document
Patent Document 1: JP-A 61-260032
Non-Patent Documents
Non-Patent Document 1: Rouzaud J. et al., Bull. Soc. Chim. Fr., 1964, 2908-2916
Non-Patent Document 2: Doucet, Rumpf, Bull. Soc. Chim. Fr., 1954, 610-613
Non-Patent Document 3: Elwin E. Harris, James D'Ianni and Homer Adkins, J. Am. Chem. Soc., 60, 1938, 1467-1470

SUMMARY OF THE INVENTION

Problems to be Solved by the Invention

An object of the present invention is to provide an industrially superior method for producing cyclohexyl alkyl ketones, which solves the problems in process reduction and in disposal of wastes such as metals and others and which has high selectivity in nuclear hydrogenation.

Means for Solving the Problems

The present inventors have assiduously studied an industrially superior method for producing cyclohexyl alkyl ketones and, as a result, have found that, when an aromatic ketone is nuclear-hydrogenated with pressurized hydrogen in the presence of a catalyst that carries a ruthenium atom, then a cyclohexyl alkyl ketone can be produced while keeping the structure of the carbonyl group therein, and have reached the present invention.

Specifically, the present invention relates to a method for producing a saturated aliphatic ketone, wherein an aromatic ketone represented by a general formula (1) is nuclear-hydrogenated with pressurized hydrogen and in the presence of a solvent at a temperature of from 20 to 120° C., in the presence of a catalyst that carries from 0.1 to 20% by weight of a ruthenium atom on the carrier, thereby producing a cyclohexyl alkyl ketone represented by a general formula (2).

[Chemical Formula 1]

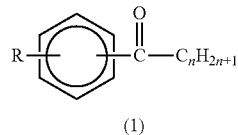

(1)

(In the general formula (1), n indicates an integer of from 1 to 3; R represents a hydroxyl group, a phenyl group, an alkyl group having from 1 to 4 carbon atoms, or an acyl group having from 1 to 4 carbon atoms.)

[Chemical Formula 2]

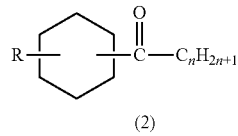

(2)

(In the general formula (2), n indicates an integer of from 1 to 3; R represents a hydroxyl group, a cyclohexyl group, an alkyl group having from 1 to 4 carbon atoms, or an acyl group having from 1 to 4 carbon atoms.)

Advantages of the Invention

According to the method of the present invention, a cyclohexyl alkyl ketone can be produced in an industrially advantageous process having high selectivity in nuclear hydrogenation.

MODE FOR CARRYING OUT THE INVENTION

[Aromatic Ketone]

The aromatic ketone to be used as the starting material in the invention is a di-substituted aromatic compound, in which, as shown by the general formula (1), a hydroxyl group, a phenyl group, an alkyl group having from 1 to 4 carbon atoms or an acyl group having from 1 to 4 carbon atoms bonds to the aromatic group as R, in addition to the acyl group bonding thereto. As R, preferred is a hydroxyl group, a phenyl group or an acyl group represented by the following general formula (3), from the viewpoint of selectively giving the intended product with no hydrogenation on the acyl group.

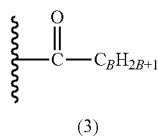

[Chemical Formula 3]

(3)

(In the general formula (3), B indicates an integer of from 1 to 3.)

In the general formula (1), n is an integer of from 1 to 3, and from the viewpoint of handling the compound in the process, n is preferably 1 or 2.

As the aromatic ketone represented by the general formula (1), specifically, there may be exemplified p-hydroxyacetophenone, m-hydroxyacetophenone, o-hydroxyacetophenone, p-hydroxypropiophenone, m-hydroxypropiophenone, o-hydroxypropiophenone, p-hydroxybutyrophenone, m-hydroxybutyrophenone, o-hydroxybutyrophenone, p-hydroxyisobutyrophenone, m-hydroxyisobutyrophenone, o-hydroxyisobutyrophenone, 2-acetylbiphenyl, 3-acetylbiphenyl, 4-acetylbiphenyl, 2-propionylbiphenyl, 3-propionylbiphenyl, 4-propionylbiphenyl, p-phenylbutyrophenone, m-phenylbutyrophenone, o-phenylbutyrophenone, p-phenylisobutyrophenone, m-phenylisobutyrophenone, o-phenylisobutyrophenone, p-methylacetophenone, m-methylacetophenone, o-methylacetophenone, p-methylpropiophenone, m-methylpropiophenone, o-methylpropiophenone, p-methylbutyrophenone, m-methylbutyrophenone, o-methylbutyrophenone, p-methylisobutyrophenone, m-methylisobutyrophenone, o-methylisobutyrophenone, p-ethylacetophenone, m-ethylacetophenone, o-ethylacetophenone, p-ethylpropiophenone, m-ethylpropiophenone, o-ethylpropiophenone, p-ethylbutyrophenone, m-ethylbutyrophenone, o-ethylbutyrophenone, p-ethylisobutyrophenone, m-ethylisobutyrophenone, o-ethylisobutyrophenone, p-propylacetophenone, m-propylacetophenone, o-propylacetophenone, 4-n-butylacetophenone, 4-i-butylacetophenone, 4-tert-butylacetophenone, 4-acetylacetophenone, 4-propionylacetophenone, and 4-acetylbutyrophenone, etc.

Of the above-mentioned aromatic ketones, preferred is hydroxyacetophenone or hydroxypropiophenone from the viewpoint of the reactivity and the use. In particular, p-hydroxyacetophenone and m-hydroxyacetophenone with the hydroxyl group bonding thereto are preferred to p-methylacetophenone with the methyl group bonding thereto and 4-acetylbiphenyl with the phenyl group bonding thereto, from the viewpoint of the reaction speed.

[Catalyst]

The catalyst for use in the present invention carries from 0.1 to 20% by weight of a ruthenium atom on the carrier thereof.

The catalyst for use in the present invention, in which the amount of the supported ruthenium atom is from 0.1 to 20% by weight, is not specifically defined in its production method. For example, the catalyst may be prepared in a method of supporting a ruthenium atom-containing compound on a carrier according to an impregnation, desiccation method, a precipitation method or the like, then processing it for reduction, for example, reduction with hydrogen or chemical reduction with sodium borohydride, hydrazine, formic acid or the like, or not processing it for reduction to prepare the intended catalyst.

In this, the ruthenium atom-containing compound includes, for example, ruthenium chloride hydrate, ruthenium bromide hydrate, ruthenium oxide hydrate, hexamine ruthenium chloride, hexamine ruthenium bromide, trinitratonitrosyl diaquaruthenium, tris(acetylacetonato)ruthenium, triruthenium dodecacarbonyl, etc.

The carrier may be any one inert to the substituents of the aromatic compound that is the starting material for hydrogenation, under the reaction condition, and may be an organic or inorganic one, including, for example, active carbon, ion-exchange resin, silica, $\alpha$-alumina, $\gamma$-alumina, silica-alumina, zeolite, as well as various types of metal oxides, composite oxides, etc. Especially preferred are alumina and active carbon from the viewpoint of the selectivity.

The amount of ruthenium to be supported on the catalyst for use in the invention falls within a range of from 0.1 to 20% by weight of the total weight of the catalyst. When the amount is less than 0.1% by weight, a large amount of the catalyst must be used for attaining a sufficient nuclear hydrogenation ratio, and the industrial use thereof would be difficult. When the amount is more than 20% by weight, then the ratio of ruthenium to be taken into the pores may increase unnecessarily, and if so, there may occur hydrogenolysis or acyl reduction in the pores where the diffusion is insufficient and the selectivity may be thereby lowered. From the viewpoints, the amount to be supported is preferably from 0.5 to 10% by weight, more preferably from 2 to 5% by weight.

The amount of the catalyst to be used in the present invention may greatly vary depending on the amount of the supported active ingredient, the type of the starting material to be hydrogenated, the reaction condition and others, but in general, the amount preferably falls within a range of from 0.05 to 0.5 in terms of the ratio by weight to the starting material, 1. From the industrial viewpoint, more preferably, the amount falls within a range of from 0.1 to 0.3.

[Hydrogenation]

According to the production method of the invention, a saturated aliphatic ketone is obtained by nuclear-hydrogenating the above-mentioned aromatic ketone represented by the general formula (1) with pressurized hydrogen in the presence of a solvent at a temperature of from 20 to 120° C.

The hydrogenation in the present invention may be attained in the absence of a solvent, depending on the type of the starting material to be hydrogenated and on the reaction condition; however, preferably, the hydrogenation is attained in the solvent from the viewpoint that the selectivity can be increased by selecting a solvent most suitable for the intended reaction and that the reaction time can be shortened.

Not specifically defined, the solvent for use herein may be a compound poorly active to the hydrogenation and capable of dissolving the starting material. As concrete examples, there may be mentioned hydrocarbons not having a double bond such as n-pentane, n-hexane, cyclohexane; ethers such as diethyl ether, dibutyl ether, tetrahydrofuran; alcohols such as methanol, ethanol, n-propanol, isopropanol, n-butanol, isobutanol, 2-butanol, tert-butanol, n-hexanol, cyclohexanol; halogenohydrocarbons such as carbon tetrachloride, dichloromethane, trichloroethane.

In the present invention, among the above-mentioned solvents, preferred are saturated aliphatic alcohols having from 2 to 5 carbon atoms, linear or branched ethers, or saturated aliphatic hydrocarbons having from 5 to 10 carbon atoms, from the viewpoint of being accompanied by side reaction and handling in production not.

The above-mentioned solvents can be used singly, or can be used as a combination of two or more of them.

Above all, preferred are diethyl ether, tetrahydrofuran, methanol, ethanol, n-propanol, cyclohexanol, cyclohexane, n-hexane, heptane; and even more preferred is tetrahydrofuran.

Not specifically defined, the ratio of the solvent to be used is, on the basis of the weight thereof, preferably within a range of from 0.05 to 100, more preferably from 0.1 to 20, in terms of ratio by weight relative to the starting material, 1.

Hydrogen to be used in the reaction may be any one generally used in industry; however, when hydrogen in which the amount of the impurity, carbon monoxide is small, is used, the catalyst activity could be excellent. Accordingly, the content of carbon monoxide in hydrogen is preferably at most 1%.

Not specifically defined, the hydrogen pressure during reaction may be in any condition under pressure; however, if too low, the reaction may take a longer time than necessary, but if too high, the hydrogen consumption rate may increase. Accordingly, the pressure preferably falls within a range of from 0.5 to 20 MPa, more preferably within a range of from 1 to 10 MPa.

The reaction temperature during the reaction may greatly vary depending on the type of the starting material to be hydrogenated, the reaction condition and the reaction time, and may be suitably defined within a range of from 0 to 200° C., but is preferably within a range of from 20 to 120° C. from the viewpoint of the selectivity and the economical aspect. Especially for the starting material having a highly-reactive substituent, the selectivity may increase when the temperature is selected preferably within a range of from 20 to 100° C., more preferably from 30 to 80° C., even more preferably from 30 to 60° C.

The reaction time for the reaction may be a time in which hydrogen absorption terminates. The time may vary depending on the type of the starting material to be hydrogenated, the amount of the catalyst and other reaction conditions, and therefore could not be indiscriminately defined. In general, the time may be from 0.5 to 20 hours.

As described above, the nuclear hydrogenation of the substituted aromatic ketone readily gives the intended hydrogenated product at high selectivity.

Specifically, the advantage of the production method is that the nuclear hydrogenation provides an extremely high selectivity.

In addition, the above-mentioned ruthenium catalyst is available extremely inexpensively. Further, the catalyst can be used repeatedly, and therefore, the nuclear hydrogenation method is a method additionally advantageous in point of reducing the catalyst cost.

Not specifically defined, the reaction equipment may be any one resistant to the necessary hydrogen pressure.

The reaction mode is preferably a batch mode from the viewpoint that the used catalyst must be separated in a liquid phase at the reaction temperature.

For example, a starting material of an aromatic ketone, a ruthenium catalyst and a solvent are fed into an autoclave equipped with an electromagnetic stirrer, then the contents are stirred and the liquid temperature is set, and thereafter the pressure is increased up to 0.5 to 20 MPa by hydrogen introduced thereinto, then under the condition where the pressure and the liquid temperature are kept as such, hydrogen is further introduced so as to keep the pressure constant, then the autoclave is kept as such until no more hydrogen is absorbed, thereafter the oil phase is collected through filtration or the like, and then analyzed through chromatography to thereby confirm the formed cyclohexyl alkyl ketone.

[Cyclohexyl Alkyl Ketones]

The present invention relates to a method for producing the saturated aliphatic ketone by which the cyclohexyl alkyl ketone represented by the above-mentioned general formula (2) is produced. In the general formula (2), n indicates an integer of from 1 to 3, R represents a hydroxyl group, a cyclohexyl group, an alkyl group having from 1 to 4 carbon atoms, or an acyl group having from 1 to 4 carbon atoms. R and n in the general formula (2) are the same as those mentioned hereinabove for the starting material aromatic ketone.

The nuclear hydrogenation product, cyclohexyl alkylketene that is obtained according to the present invention could be the intended product having a high purity even though the catalyst is removed through filtration or the like and then the solvent alone is merely removed; however, if desired, the product can be further purified according to a conventional known method of distillation, crystallization or the like. The catalyst recovered at this time can be reused for reaction.

The selectivity of the cyclohexyl alkyl ketone obtained according to the production method of the present invention is higher than in conventional methods, and is generally at least 50%, preferably at least 60%, more preferably at least 85%, even more preferably at least 90%, still more preferably at least 95%.

The yield of the cyclohexyl alkyl ketone may be generally at least 50%, but is preferably at least 60%, more preferably at least 85%, even more preferably at least 90%, still more preferably at least 95%.

EXAMPLES

The present invention will be described more specifically below, but the present invention is not restricted by the examples.

<Conditions of Gas Chromatography Analysis>

The reaction results were evaluated through gas chromatography. In gas chromatography, used was GC-17A available from Shimadzu Corporation with a capillary column, HR-1 (0.32 mmφ×25 m) available from Shinwa Chemical Industries Ltd. Regarding the heating condition, the system was heated from 100° C. up to 320° C. at a rate of 5° C./min. The cis/trans isomer ratio of the cyclohexane ring was determined, using capillary column, Xylene Master (0.32 mmφ× 50 m) available from Shinwa Chemical Industries Ltd. Regarding the heating condition, the system was heated from 70° C. up to 120° C. at a rate of 2° C./min.

Example 1

[Chemical Formula 4]

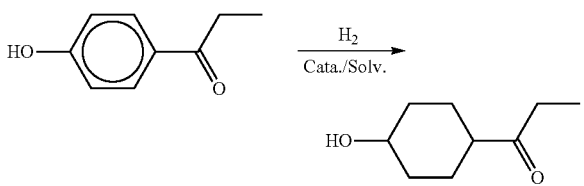

2 g of 5% Ru/alumina catalyst available from N.E. CHEMCAT, 10 g of p-hydroxypropiophenone (chemical reagent available from Wako Pure Chemicals), and 100 ml of tetrahydrofuran (chemical reagent available from Wako Pure Chemicals) were put into a 200-ml autoclave reactor, the gas inside the reactor was purged with nitrogen gas, the reactor was set at 50° C., then hydrogen was added thereto so that the pressure in the reactor could be 4 MPa, and the reaction was continued for 5 hours until the hydrogen supply was stopped. After the reaction, the catalyst was removed through filtration, and the resulting filtrate was analyzed through gas chromatography. The starting material conversion was confirmed to be 100%, the selectivity of 4-propionylcyclohexanol was 98%, and the yield was 98%. The cis/trans isomer ratio of the cyclohexane ring was 64/36.

Example 2

The hydrogenation and the reaction liquid treatment were carried out in the same manner as in Example 1, except that the solvent was ethanol (chemical reagent available from Wako Pure Chemicals). After the reaction, the catalyst was removed through filtration, and the resulting filtrate was analyzed through gas chromatography. The starting material conversion was confirmed to be 100%, the selectivity of 4-propionylcyclohexanol was 96%, and the yield was 96%. The cis/trans isomer ratio of the cyclohexane ring was 64/36.

Example 3

The hydrogenation and the reaction liquid treatment were carried out in the same manner as in Example 1, except that the solvent was methanol (chemical reagent available from Wako Pure Chemicals). After the reaction, the catalyst was removed through filtration, and the resulting filtrate was analyzed through gas chromatography. The starting material conversion was confirmed to be 100%, the selectivity of 4-propionylcyclohexanol was 96%, and the yield was 96%. The cis/trans isomer ratio of the cyclohexane ring was 66/34.

Example 4

The hydrogenation and the reaction liquid treatment were carried out in the same manner as in Example 1, except that the solvent was n-butanol (chemical reagent available from Wako Pure Chemicals) and the reaction time was 9 hours. After the reaction, the catalyst was removed through filtration, and the resulting filtrate was analyzed through gas chromatography. The starting material conversion was confirmed to be 100%, the selectivity of 4-propionylcyclohexanol was 89%, and the yield was 89%. The cis/trans isomer ratio of the cyclohexane ring was 64/36.

Example 5

The hydrogenation and the reaction liquid treatment were carried out in the same manner as in Example 1, except that the catalyst used in Example 1 was reused here. After the reaction, the catalyst was removed through filtration, and the resulting filtrate was analyzed through gas chromatography. The starting material conversion was confirmed to be 100%, the selectivity of 4-propionylcyclohexanol was 93%, and the yield was 93%. The cis/trans isomer ratio of the cyclohexane ring was 66/34.

Example 6

70 g of 5% Ru/alumina catalyst available from N.E. CHEMCAT, 350 g of p-hydroxypropiophenone and 1750 ml of ethanol were put into a 10-liter autoclave reactor, the gas inside the reactor was purged with nitrogen gas, the reactor was set at 50° C., then hydrogen was added thereto so that the pressure in the reactor could be 4 MPa, and the reaction was continued for 10 hours until the hydrogen supply was stopped. After the reaction, the catalyst was removed through filtration, and the resulting filtrate was analyzed through gas chromatography. The starting material conversion was confirmed to be 100%, the selectivity of 4-propionylcyclohexanol was 93%, and the yield was 93%. The cis/trans isomer ratio of the cyclohexane ring was 64/36.

Example 7

The hydrogenation and the reaction liquid treatment were carried out in the same manner as in Example 1, except that 5% Ru/carbon (hydrate) A Type catalyst available from N.E. CHEMCAT was used in place of the 5% Ru/alumina catalyst used in Example 1, and the reaction time was 6 hours. After the reaction, the catalyst was removed through filtration, and the resulting filtrate was analyzed through gas chromatography. The starting material conversion was confirmed to be 100%, the selectivity of 4-propionylcyclohexanol was 54%, and the yield was 54%. The cis/trans isomer ratio of the cyclohexane ring was 69/31.

Example 8

The hydrogenation and the reaction liquid treatment were carried out in the same manner as in Example 1, except that 5% Ru/carbon (hydrate) B Type catalyst available from N.E. CHEMCAT was used in place of the 5% Ru/alumina catalyst used in Example 1, and the reaction time was 6 hours. After the reaction, the catalyst was removed through filtration, and the resulting filtrate was analyzed through gas chromatography. The starting material conversion was confirmed to be 100%, the selectivity of 4-propionylcyclohexanol was 90%, and the yield was 90%. The cis/trans isomer ratio of the cyclohexane ring was 64/36.

Example 9

The hydrogenation and the reaction liquid treatment were carried out in the same manner as in Example 1, except that 5% Ru/carbon (hydrate) K Type catalyst available from N.E. CHEMCAT was used in place of the 5% Ru/alumina catalyst used in Example 1, and the reaction time was 6 hours. After the reaction, the catalyst was removed through filtration, and the resulting filtrate was analyzed through gas chromatography. The starting material conversion was confirmed to be 100%, the selectivity of 4-propionylcyclohexanol was 60%, and the yield was 60%. The cis/trans isomer ratio of the cyclohexane ring was 67/33.

Example 10

The hydrogenation and the reaction liquid treatment were carried out in the same manner as in Example 1, except that 5% Ru/carbon (hydrate) R Type catalyst available from N.E. CHEMCAT was used in place of the 5% Ru/alumina catalyst used in Example 1, and the reaction time was 6 hours. After the reaction, the catalyst was removed through filtration, and the resulting filtrate was analyzed through gas chromatography. The starting material conversion was confirmed to be 100%, the selectivity of 4-propionylcyclohexanol was 90%, and the yield was 90%. The cis/trans isomer ratio of the cyclohexane ring was 68/32.

Example 11

[Chemical Formula 5]

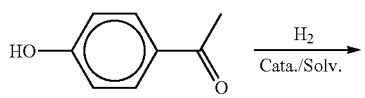

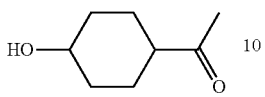

The hydrogenation and the reaction liquid treatment were carried out in the same manner as in Example 2, except that p-hydroxyacetophenone (chemical reagent available from Wako Pure Chemicals) was used in place of p-hydroxypropiophenone used in Example 2 and the reaction time was 4 hours. After the reaction, the catalyst was removed through filtration, and the resulting filtrate was analyzed through gas chromatography. The starting material conversion was confirmed to be 100%, the selectivity of 4-acetylcyclohexanol was 96%, and the yield was 96%. The cis/trans isomer ratio of the cyclohexane ring was 64/36.

Example 12

[Chemical Formula 6]

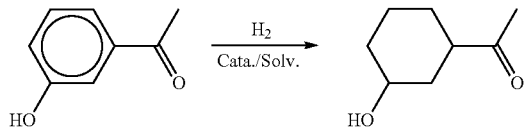

The hydrogenation and the reaction liquid treatment were carried out in the same manner as in Example 2, except that m-hydroxyacetophenone (chemical reagent available from Wako Pure Chemicals) was used in place of p-hydroxypropiophenone used in Example 2 and the reaction time was 5 hours. After the reaction, the catalyst was removed through filtration, and the resulting filtrate was analyzed through gas chromatography. The starting material conversion was confirmed to be 100%, the selectivity of 3-acetylcyclohexanol was 97%, and the yield was 97%. The cis/trans isomer ratio of the cyclohexane ring was 40/60.

Example 13

[Chemical Formula 7]

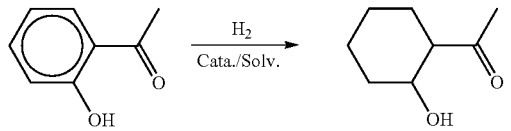

The hydrogenation and the reaction liquid treatment were carried out in the same manner as in Example 2, except that o-hydroxyacetophenone (chemical reagent available from Wako Pure Chemicals) was used in place of p-hydroxypropiophenone used in Example 2 and the reaction time was 5 hours. After the reaction, the catalyst was removed through filtration, and the resulting filtrate was analyzed through gas chromatography. The starting material conversion was confirmed to be 100%, the selectivity of 2-acetylcyclohexanol was 96%, and the yield was 96%. The cis/trans isomer ratio of the cyclohexane ring was 60/40.

Example 14

[Chemical Formula 8]

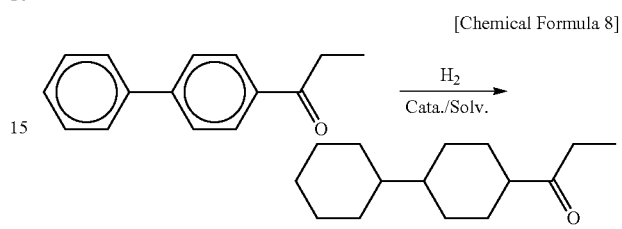

The hydrogenation and the reaction liquid treatment were carried out in the same manner as in Example 2, except that 4-propionyl-1,1'-biphenyl (chemical reagent available from Tokyo Chemical Industry) was used in place of p-hydroxypropiophenone used in Example 2 and the reaction time was 11 hours. After the reaction, the catalyst was removed through filtration, and the resulting filtrate was analyzed through gas chromatography. The starting material conversion was confirmed to be 100%, the selectivity of 4-propionyl-1,1'-bicyclohexane was 96%, and the yield was 96%. The cis/trans isomer ratio of the cyclohexane ring was 72/28.

Example 15

The hydrogenation and the reaction liquid treatment were carried out in the same manner as in Example 14, except that the solvent was heptane (chemical reagent available from Wako Pure Chemicals) and the reaction time was 10 hours. After the reaction, the catalyst was removed through filtration, and the resulting filtrate was analyzed through gas chromatography. The starting material conversion was confirmed to be 100%, the selectivity of 4-propionyl-1,1'-bicyclohexane was 96%, and the yield was 96%. The cis/trans isomer ratio of the cyclohexane ring was 72/28.

Example 16

[Chemical Formula 9]

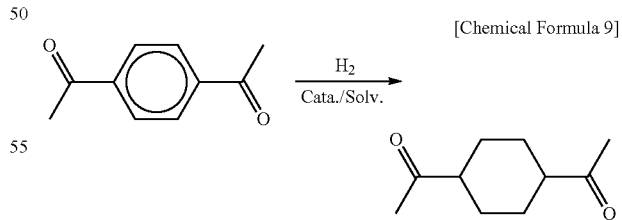

The hydrogenation and the reaction liquid treatment were carried out in the same manner as in Example 2, except that 1,4-diacetylbenzene (chemical reagent available from Tokyo Chemical Industry) was used in place of p-hydroxypropiophenone used in Example 2. After the reaction, the catalyst was removed through filtration, and the resulting filtrate was analyzed through gas chromatography. The starting material conversion was confirmed to be 100%, the selectivity of 1,4- diacetylcyclohexane was 97%, and the yield was 97%. The cis/trans isomer ratio of the cyclohexane ring was 76/24.

Example 17

[Chemical Formula 10]

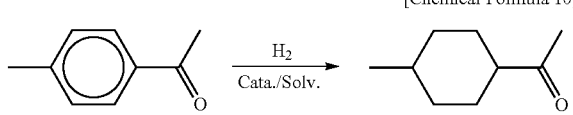

The hydrogenation and the reaction liquid treatment were carried out in the same manner as in Example 2, except that 4'-methylacetophenone (chemical reagent available from Wako Pure Chemicals) was used in place of p-hydroxypropiophenone used in Example 2 and the reaction time was 6 hours. After the reaction, the catalyst was removed through filtration, and the resulting filtrate was analyzed through gas chromatography. The starting material conversion was confirmed to be 100%, the selectivity of 1-acetyl-4-methylcyclohexane was 96%, and the yield was 96%. The cis/trans isomer ratio of the cyclohexane ring was 22/78.

Comparative Example 1

[Chemical Formula 11]

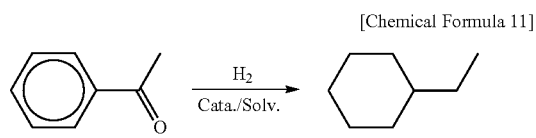

The hydrogenation and the reaction liquid treatment were carried out in the same manner as in Example 2, except that acetophenone was used in place of p-hydroxypropiophenone used in Example 2 and the reaction time was 6 hours. After the reaction, the catalyst was removed through filtration, and the resulting filtrate was analyzed through gas chromatography. The starting material conversion was confirmed to be 100%, and the selectivity of ethylcyclohexane was 99%.

Comparative Example 2

[Chemical Formula 12]

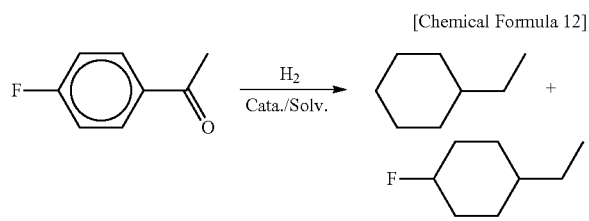

The hydrogenation and the reaction liquid treatment were carried out in the same manner as in Example 2, except that 4'-fluoroacetophenone (chemical reagent available from Wako Pure Chemicals) was used in place of p-hydroxypropiophenone used in Example 2 and the reaction time was 3.5 hours. After the reaction, the catalyst was removed through filtration, and the resulting filtrate was analyzed through gas chromatography. The starting material conversion was confirmed to be 100%, the selectivity of ethylcyclohexane was 74%, and the selectivity of 1-ethyl-4-fluorocyclohexane was 26%.

Comparative Example 3

[Chemical Formula 13]

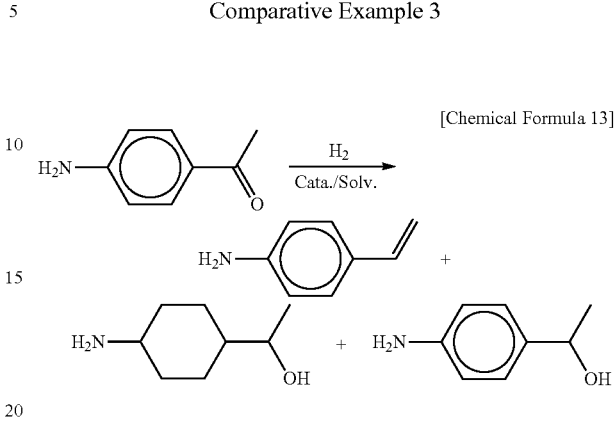

The hydrogenation and the reaction liquid treatment were carried out in the same manner as in Example 2, except that p-aminoacetophenone (chemical reagent available from Wako Pure Chemicals) was used in place of p-hydroxypropiophenone used in Example 2. After the reaction, the catalyst was removed through filtration, and the resulting filtrate was analyzed through gas chromatography. The starting material conversion was confirmed to be 58%, and the reaction liquid was a mixed liquid of 4-amino-1-vinylbenzene (selectivity 22%), 1-(4-aminocyclohexyl)ethanol (selectivity 27%), and 1-(4-aminophenyl)ethanol (selectivity 41%).

Comparative Example 4

The hydrogenation and the reaction liquid treatment were carried out in the same manner as in Example 1, except that a copper chromium catalyst (203S) available from JGC Catalysts and Chemicals was used in place of the 5% Ru/alumina catalyst used in Example 1, the reaction time was 3 hours and the reaction temperature was 140° C. After the reaction, the catalyst was removed through filtration, and the resulting filtrate was analyzed through gas chromatography. The starting material conversion was confirmed to be 100%, the selectivity of 4-propionylcyclohexanol was 0%, and the selectivity of 4-propylphenol was 100%.

Comparative Example 5

The hydrogenation and the reaction liquid treatment were carried out in the same manner as in Example 1, except that 2% Rh/carbon catalyst (hydrate) available from N.E. CHEMCAT was used in place of the 5% Ru/alumina catalyst used in Example 1, the reaction time was 2 hours and the reaction temperature was 140° C. After the reaction, the catalyst was removed through filtration, and the resulting filtrate was analyzed through gas chromatography. The starting material conversion was confirmed to be 100%, the selectivity of 4-propionylcyclohexanol was 0%, and the selectivity of 4-propylcyclohexanol was 93%. The cis/trans isomer ratio of the cyclohexane ring of 4-propylcyclohexanol was 53/47.

Comparative Example 6

The hydrogenation and the reaction liquid treatment were carried out in the same manner as in Example 1, except that 5% Pd/carbon catalyst (hydrate) STD Type available from N.E. CHEMCAT was used in place of the 5% Ru/alumina catalyst used in Example 1, the reaction temperature was 140° C., and the solvent was cyclohexane. After the reaction, the catalyst was removed through filtration, and the resulting filtrate was analyzed through gas chromatography. The starting material conversion was confirmed to be 100%, the selectivity of 4-propionylcyclohexanol was 0%, and the selectivity of 4-propylcyclohexanol was 95%. The cis/trans isomer ratio of the cyclohexane ring of 4-propylcyclohexanol was 55/45.

Comparative Example 7

The hydrogenation and the reaction liquid treatment were carried out in the same manner as in Example 7, except that the temperature was 140° C. After the reaction, the catalyst was removed through filtration, and the resulting filtrate was analyzed through gas chromatography. The starting material conversion was confirmed to be 100%, the selectivity of 4-propionylcyclohexanol was 14%, and the selectivity of 4-propylcyclohexanol was 82%.

INDUSTRIAL APPLICABILITY

Cyclohexyl alkyl ketones obtained in the present invention are useful as starting materials for dyes, fragrances, medicines, agricultural chemicals, electronic functional materials and optical functional materials.

The invention claimed is:

1. A method for producing a saturated aliphatic ketone, the method comprising hydrogenating an aromatic ketone represented by formula (1) with pressurized hydrogen in the presence of a solvent at a temperature of from 20 to 120° C. and a catalyst comprising from 0.1 to 20% by weight of ruthenium on a carrier, to produce a cyclohexyl alkyl ketone represented by formula (2):

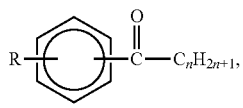 (1)

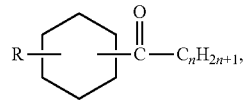 (2)

wherein:

n represents an integer of from 1 to 3; and

R represents a hydroxyl group, a phenyl group, an alkyl group having from 1 to 4 carbon atoms, or an acyl group having from 1 to 4 carbon atoms.

2. The method of claim 1, wherein the carrier is alumina or active carbon.

3. The method of claim 2, wherein the carrier is alumina.

4. The method of claim 1, wherein the aromatic ketone represented by formula (1) is p-hydroxyacetophenone or hydroxypropiophenone.

5. The method of claim 1, wherein the solvent is a saturated aliphatic alcohol having from 2 to 5 carbon atoms, a linear or cyclic ether, or a saturated aliphatic hydrocarbon having from 5 to 10 carbon atoms.

6. The method of claim 1, wherein the pressure of hydrogen is from 0.5 to 20 MPa.

7. The method of claim 2, wherein the aromatic ketone represented by formula (1) is p-hydroxyacetophenone or hydroxypropiophenone.

8. The method of claim 3, wherein the aromatic ketone represented by formula (1) is p-hydroxyacetophenone or hydroxypropiophenone.

9. The method of claim 2, wherein the solvent is a saturated aliphatic alcohol having from 2 to 5 carbon atoms, a linear or cyclic ether, or a saturated aliphatic hydrocarbon having from 5 to 10 carbon atoms.

10. The method of claim 3, wherein the solvent is a saturated aliphatic alcohol having from 2 to 5 carbon atoms, a linear or cyclic ether, or a saturated aliphatic hydrocarbon having from 5 to 10 carbon atoms.

11. The method of claim 2, wherein the pressure of hydrogen is from 0.5 to 20 MPa.

12. The method of claim 3, wherein the pressure of hydrogen is from 0.5 to 20 MPa.

* * * * *